United States Patent
Fong et al.

(10) Patent No.: US 7,041,864 B2
(45) Date of Patent: May 9, 2006

(54) LINEAR AND BRANCHED OLEFIN PRODUCTION FROM CYCLIC OLEFIN FEEDSTOCKS

(75) Inventors: Howard Lam-ho Fong, Sugar Land, TX (US); Michael Wayne Potter, Sugar Land, TX (US); David Stephen Brown, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 548 days.

(21) Appl. No.: 10/316,812

(22) Filed: Dec. 11, 2002

(65) Prior Publication Data

US 2004/0116763 A1   Jun. 17, 2004

(51) Int. Cl.
*C07C 6/00* (2006.01)

(52) U.S. Cl. .................. 585/646; 585/643; 585/647

(58) Field of Classification Search .......... 585/643, 585/646, 647
See application file for complete search history.

(56) References Cited

U.S. PATENT DOCUMENTS

| | | | |
|---|---|---|---|
| 3,575,947 A | 4/1971 | Crain | 260/93.1 |
| 4,454,368 A * | 6/1984 | Banks | 585/646 |
| 4,709,115 A * | 11/1987 | Jung et al. | 585/643 |
| 5,254,786 A * | 10/1993 | Lin et al. | 585/645 |
| 5,898,091 A * | 4/1999 | Chodorge et al. | 585/647 |
| 6,388,162 B1 * | 5/2002 | Himelfarb et al. | 585/809 |

FOREIGN PATENT DOCUMENTS

| | | |
|---|---|---|
| WO | WO 01/05735 A1 | 1/2001 |
| WO | WO 02/079127 A1 | 10/2002 |

OTHER PUBLICATIONS

"Running the 'Impossible' Reaction, Metathesis of Cyclohexene," by Penelope A. Patton and Thomas J. McCarthy, CHEMTECH Jul. 1987, pp. 442-446.

"Synthesis and Investigation of Homo- and Heterobimetallic Ruthenium Olefin Metathesis Catalysts Exhibiting Increased Activities," by Eric L. Dias and Robert H. Grubbs, Organometallics 1998, 17, pp. 2758-2767.

International Search Report of Jun. 4, 2004.

* cited by examiner

*Primary Examiner*—Walter D. Griffin
*Assistant Examiner*—In Suk Bullock

(57) ABSTRACT

Ring opening cross metathesis of secondary non-cyclic hydrocarbons with cyclic unsaturated hydrocarbons having 8 carbon atoms or more to produce corresponding unsaturated product hydrocarbons having more than 8 carbon atoms.

195 Claims, 2 Drawing Sheets

LINEAR AND BRANCHED OLEFIN PRODUCTION FROM CYCLIC OLEFIN FEEDSTOCKS

FIELD OF THE APPLICATION

The application relates to methods for using ring opening cross metathesis of non-cyclic hydrocarbons with cyclic unsaturated hydrocarbons having 8 carbon atoms or more to produce corresponding unsaturated product hydrocarbons having more than 8 carbon atoms. The process preferably is tailored to produce multi-unsaturated product hydrocarbons having from about 10 to about 16 carbon atoms, more preferably from about 11 to about 14 carbon atoms. The multi-unsaturated product hydrocarbons are useful as intermediates to make a wide variety of products, particularly surfactants, more particularly alcohols, most particularly mono-hydroxy saturated alcohols useful to produce a variety of detergent products.

BACKGROUND OF THE INVENTION

Common methods for producing higher olefins typically use relatively expensive lower olefins as starting materials. Methods are needed to produce higher olefins using inexpensive feedstocks, particularly byproducts from refinery processes, which otherwise might have little economic value.

SUMMARY OF THE INVENTION

The present application provides a method for making unsaturated hydrocarbons, said method comprising:
  providing a mixture comprising one or more cyclic unsaturated hydrocarbons and an excess of one or more non-cyclic unsaturated hydrocarbons, said cyclic unsaturated hydrocarbons having a $\Delta G$ at 25° C. of less than 0 and comprising a ring structure comprising x carbon atoms and;
  exposing said mixture to conditions effective to cross metathesize said cyclic unsaturated hydrocarbons with said one or more non-cyclic unsaturated hydrocarbons to produce primarily non-cyclic unsaturated product hydrocarbons comprising a single molecule of said cyclic unsaturated hydrocarbons and having more than x carbon atoms

DETAILED DESCRIPTION

Figure 1:
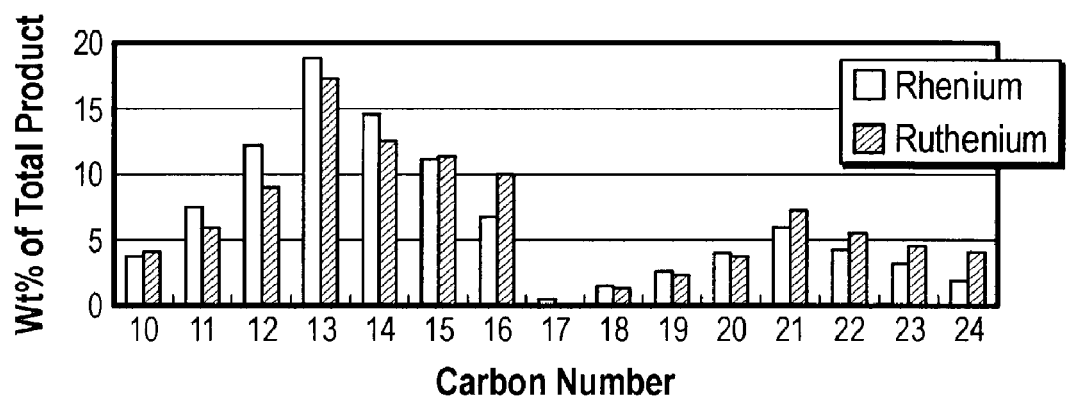
FIG. 1 is a graph depicting the wt. % of total product vs. the carbon number of the product from the cross metathesis of cyclooctene with pentenes (Example 7).

The present application provides methods for using ring opening cross-metathesis (ROM) to produce linear and/or branched unsaturated product hydrocarbons. The method cross metathesizes cyclic unsaturated hydrocarbons ("cyclic-HC's") with non-cyclic unsaturated linear and/or branched hydrocarbons ("non-cyclic-HC's"). The product hydrocarbons comprise primarily non-cyclic unsaturated product hydrocarbons comprising a single cyclic unsaturated hydrocarbon, said product hydrocarbons having more than 8 carbon atoms. The process is extremely economical, produces excellent selectivity, and can be focused to produce primarily non-cyclic-HC's having a selected number of carbon atoms. In a preferred embodiment, the process is tailored to produce non-cyclic-HC's having from about 10 to about 16 carbon atoms, more preferably from about 11 to about 14 carbon atoms. In another embodiment, the process is tailored to produce product hydrocarbons having a combination of 15 and 16 carbon atoms.

Although ROM can be performed using high value non-cyclic-HC's, such as ethylene or propylene, ROM has the advantage that it is effective using low-value feeds, particularly feeds which are readily available as by-products from refinery processes.

The Cyclic-HC's

Suitable cyclic-HC's for use in the cross-metathesis reaction are unsaturated cyclic hydrocarbons comprising a ring structure having 8 carbon atoms or more, preferably having from about 8 to about 12 carbon atoms, more preferably having 8 carbon atoms or having 12 carbon atoms, most preferably having 8 carbon atoms. The cyclic-HC's may be mono- or multi-unsaturated. Monounsaturated cyclic hydrocarbons also are called "cyclic olefins." Diunsaturated cyclic hydrocarbons are called cyclic diolefins or cyclodienes, and so forth. The cyclic HC's may be substituted or unsubstituted, as long as the substituent is of a size, type, and location that does not interfere with cross metathesis and/or the desired product distribution. Methyl substituted cyclic-HC's may be suitable, for example, for producing lightly branched products. In order to avoid interference with the metathesis reaction, the substituents, preferably methyl groups, are on saturated carbons rather than on unsaturated carbons.

Suitable cyclic-HC's have a relatively low free energy change for the ring opening metathesis polymerization reaction ($\Delta G$). At 25° C., $\Delta G$ preferably is 0 kcal/mol or below, more preferably less than 0 kcal/mol, more preferably -1 kcal/mol or less, even more preferably -2 kcal/mol or less, most preferably -3 kcal/mol or less. The following are the $\Delta G$ for some common cyclic olefins at 25° C.:

$\Delta G$ for cyclopentene: -0.62 kcal/mol at 25° C.
  $\Delta G$ for cyclohexene: 1.7 kcal/mol at 25° C.
  $\Delta G$ for cyclooctene: -3.1 kcal/mol at 25° C.

Persons of ordinary skill in the art will be able to ascertain $\Delta G$ at 25° C. for other cyclic-HC's, for example, by referring to K. J. Ivin and J. C. Mol, *Olefin Metathesis and Metathesis Polymerization*, Ch. 11 "Ring-Opening Metathesis Polymerization: General Aspects" (Academic Press 1997) pp. 224–226, incorporated herein by reference.

Preferred cyclic-HC's are cyclooctenes and cyclododecenes. A most preferred cyclic-HC is cyclooctene. Substituted cyclooctenes and cyclododecenes also are suitable if (a) the substituent does not interfere with cross metathesis and/or the desired product distribution, and (b) $\Delta G$ at 25° C. is 0 kcal/mol or below, preferably less than 0 kcal/mol, more preferably -1 kcal/mol or less, even more preferably -2 kcal/mol or less, and most preferably -3 kcal/mol or less Cyclooctene and cyclododecene are commercially available, for example, from Aldrich Chemical Co. A preferred source of cyclooctene is from butadiene cyclodimerization using known processes. Exemplary processes for cyclodimerization of butadiene are described in U.S. Pat. No. 3,261,875 and U.S. Pat. No. 3,535,397, incorporated herein by reference. A preferred source of cyclododecene is from butadiene cyclotrimerization. An exemplary process for cyclotrimerization of butadiene is described in U.S. Pat. No. 6,403,851, incorporated herein by reference.

Non-Cyclic-HC's

The non-cyclic unsaturated hydrocarbon ("non-cyclic-HC") is substantially any linear or branched unsaturated hydrocarbon. Preferred non-cyclic-HC's have from about 4 to about 8 carbon atoms, preferably from about 4 to about 6 carbon atoms, most preferably 4 carbon atoms. The non-cyclic-HC may be mono- or multi-unsaturated. Mono-unsaturated hydrocarbons (olefins) generally are preferred, most preferably mono-unsaturated linear hydrocarbons, or olefins. The non-cyclic-HC may be alpha olefin and/or internal olefin, depending upon the desired product distribution. A most preferred non-cyclic-HC for producing detergent range products is 2-butene, an internal olefin.

The non-cyclic-HC may be derived from a number of sources. From an environmental and economic standpoint, preferred sources are byproducts of refinery processes. A preferred source for pentene is the C5 cut from a fluid catalytic cracker ("FCC C5's"). Butenes may be purchased from a number of sources. A preferred source for butenes is raffinate from a C4 stream from an olefin cracker, which comprises 1-butene, 2-butene, and butane (hereinafter "$C_4$ raffinate"). In a preferred embodiment, the $C_4$ raffinate is isomerized before cross-metathesis to produce primarily 2-butene.

ROM Catalyst

The cyclic-HOC's are cross metathesized with the non-cyclic-HOC's in the presence of a "ROM catalyst." Suitable "ROM catalysts" include any known olefin metathesis catalyst, examples of which are described in WO 01/05735, incorporated herein by reference. Suitable catalysts include homogeneous and heterogeneous catalyst systems. Due primarily to ease of separation of the final product, preferred catalysts are heterogeneous.

ROM catalysts suitably comprise one or more a metals selected from the group consisting of Cr, Mo, W, Mn, Tc, Re, Fe, Ru, Os. Preferably, the ROM catalyst comprises one or more metal selected from the group consisting of Mo, W, Re, and Ru, more preferably a metal selected from the group consisting of Re and Ru. Most preferably, the ROM catalyst comprises Re.

Heterogeneous ROM catalysts comprise one or more metals on a suitable support. Although the surface area of the support is not an essential feature, the surface area preferably is at least about 50 $m^2$/g in order to provide sufficient contact between the metal and the reactants in the feed. In a preferred embodiment, the support has a surface area of from about 200 $m^2$/g to 400 $m^2$/g. Suitable support materials are acidic or neutral, preferably neutral. Suitable support materials include, but are not necessarily limited to alumina, silica, molecular sieves, such as zeolites, activated carbon, aluminosilicate clays, amorphous silicoaluminas, and the like. Preferred supports are aluminum oxide (for Mo and Re) and silicon oxide (for W).

It is preferred for the support particles to be as small as possible; however, if the size of the particles is too small, the pressure drop through a bed of the particles may become too large. Very small particles also are difficult to retain in a bed. The support particles may have substantially any form, including but not necessarily limited to spherical form, tablet form, cylindrical form, multi-lobed cylindrical forms, and their corresponding hollow counterparts.

The metal may be deposited onto the support using any suitable technique, including but not necessarily limited to ion exchange, co-mulling, or impregnation. Persons of ordinary skill in the art will be able to determine a suitable known technique for incorporating the metal(s) and for calculating how to incorporate a given wt % of metal(s) onto the support.

A most preferred catalyst is Re/$Al_2O_3$ comprising Re at a concentration of from about 1 to about 20% wt %, preferably from about 5 to about 12 wt. %, more preferably at about 10 wt %.

Suitable homogeneous catalysts for ROM comprise the same metal(s) as the heterogeneous catalysts. Suitable homogeneous catalysts include, but are not necessarily limited to "Grubbs" catalysts, Schrock catalysts, and a variety of tungsten (W) based catalysts. The following are examples of suitable Grubbs catalysts:

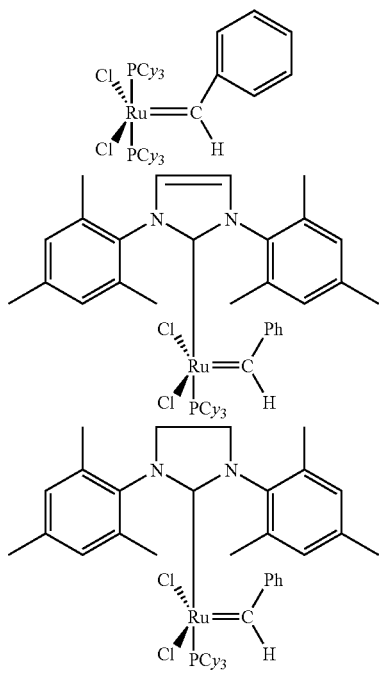

The foregoing Grubbs catalysts are commercially available, for example, from Strem Chemicals and Aldrich Chemicals. Schrock catalysts (based on Mo) are commercially available from Strem Chemicals. Suitable W-based metathesis catalyst precursors and activators also are available from Strem Chemicals. An example of a W-based metathesis catalyst precursor is a tungsten halide, such as tungsten hexachloride. Suitable activators include, but are not necessarily limited to alkyl metals, such as the promoters listed below. Preferred activators are alkyl aluminums, preferably trialkyl aluminums.

ROM Process Conditions

The cyclic-HC is fed to a suitable reactor with an excess of the selected non-cyclic-HC. Suitable reactors include any reactor suitable for use with the selected catalyst. Where the catalyst is heterogeneous, suitable reactors comprise a fixed bed, a moving bed, a downflow, an upflow, a concurrent flow, a countercurrent flow, and a catalytic distillation column, etc. Where the catalyst is homogeneous, suitable reactors include, for example, a continuous stir tank reactor.

A promoter preferably is used to activate the catalyst. The catalyst may be exposed to the promoter using any suitable means. For example, the catalyst may be activated before it is fed to the reactor. Alternately, the promoter may be fed to the reactor along with the feed. Suitable promoters include, but are not necessarily limited to alkyls of elements selected from the group consisting of B, Al, Ga, In, Tl, C, Si, Ge, Sn, Pb, N, P, As, Sb, and Bi. Preferred promoters are selected from alkyls of B, Al, Sn, and Si. More preferred promoters are alkylboranes and alkyltins. The number of alkyl groups will depend primarily on the valence of the metal. A most preferred promoter is tetrabutyltin. The amount of promoter used should be sufficient to activate the particular catalyst under the particular conditions of exposure to the promoter. The concentration of the promoter will depend upon the catalyst, the time at which the catalyst is exposed to the promoter, and other variables. Where the promoter is fed to the reactor with the cyclic-HC, the concentration of the promoter in the cyclic-HC ranges from about 1 ppm to about 10,000 ppm, preferably about 2500 ppm.

The product distribution is controlled by limiting the number of rings added to each molecule of the non-cyclic-HC. This is achieved by maintaining an excess of non-cyclic HC and controlling the ratio of non-cyclic-HC:cyclic-HC in the feed. The non-cyclic-HC:cyclic HC feed ratio is sufficiently high to achieve a desired selectivity without causing gross oversizing of the reactor. In order to produce desired detergent range products, the molar ratio of non-cyclic-HC: cyclic-HC suitably is from about 20:1 to about 1:1, preferably from about 5:1 to about 3:1, and most preferably about 3:1.

In a preferred embodiment, the LHSV for the cyclic-HC is from about 1 hr$^{-1}$ to about 10 hr$^{-1}$, most preferably about 2 hr$^{-1}$. The flow rate of the non-cyclic-HC is variable depending upon the flow rate of the cyclic-HC, and is adjusted to achieve the molar ratios given above. Conversion of the cyclic-HC's could be increased (to 100%) by reducing the flow rate or increasing the catalyst loading.

The process temperature varies depending upon the catalyst. Where the catalyst comprises Re, preferred temperatures are from about 0° C. to about 100° C., preferably from about 30° C. to about 35° C. Where the catalyst is molybdenum on aluminum oxide, preferred temperatures are from about 50° C. to about 200° C., preferably about from about 120° C. to about 150° C.

The pressure preferably is maintained at about 15 psig (or about 1 atm) or more, more preferably about 200 psig, using substantially any inert gas, "low activity" gas, or combination thereof. Suitable gases include, but are not necessarily limited to He, Ne, Ar, $N_2$, $CO_2$, and $CH_4$.

Multi-Unsaturated Hydrocarbon Products

ROM is controllable to produce hydrocarbon products having primarily selected chain lengths and comprising: (a) linear or branched multi-olefins comprising an unsaturated carbon-carbon bond in the alpha, or terminal position of the carbon backbone; and, (b) linear or branched multi-olefins comprising or even consisting essentially of unsaturated carbon-carbon bonds in positions other than the alpha position. Where the product hydrocarbons are branched, the product hydrocarbons preferably have from about 1 to about 2 branches having from about 1 to about 2 carbon atoms. More preferably, branched product hydrocarbons have 1 methyl substituent.

The metathesis reaction preferably is tailored to produce unsaturated product hydrocarbons having from about 10 to about 16 carbon atoms, more preferably from about 11 to about 14 carbon atoms. The cross metathesis product typically is multi-unsaturated.

The following diagram illustrates the product distribution from cross metathesis of 2-butene with cyclooctene:

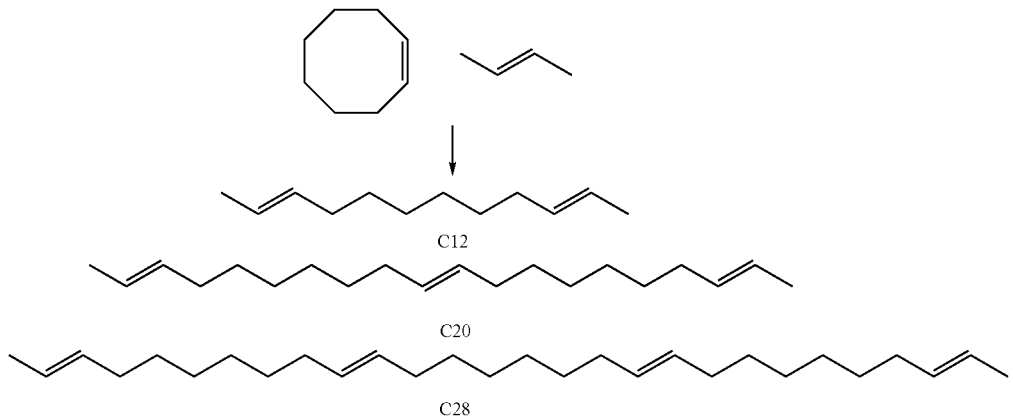

The following diagram illustrates the product distribution from cross metathesis of 2-butene and 1-butene with cyclododecene:

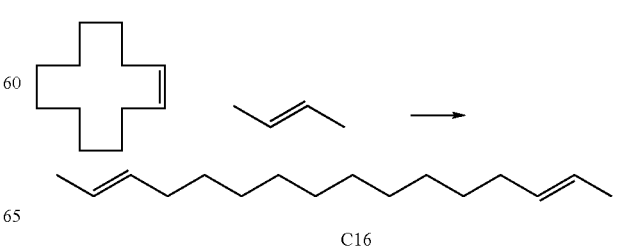

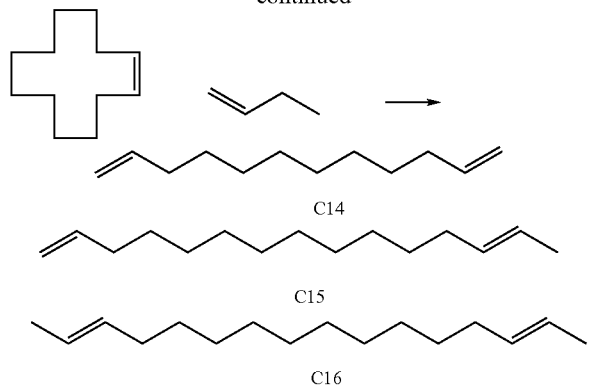

Hydrogenation

The cross-metathesis product typically is a diene or a triene. Hydroformylation of dienes or trienes yields mostly mono-alcohols. The dienes or trienes also may be hydrogenated, to reduce the total number of unsaturated carbon-carbon bonds. Hydrogenation may be performed using any available procedure. In a preferred procedure, one or more of the unsaturated carbon-carbon bonds preferably is/are selectively hydrogenated, leaving a mono-olefin. A preferred process for selective hydrogenation is described in U.S. Pat. No. 6,388,162, incorporated herein by reference.

Hydroformylation

In a preferred embodiment, the product non-cyclic unsaturated hydrocarbons, either before or after hydrogenation, are hydroformylated. Hydroformylation is a term used in the art to denote the reaction of an olefin with CO and $H_2$ to produce an aldehyde/alcohol which has one more carbon atom than the reactant olefin. Frequently, the term hydroformylation is used to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols from the multi-unsaturated hydrocarbon product of cross metathesis.

Illustrative hydroformylation catalysts include, but are not necessarily limited to, cobalt hydrocarbonyl catalysts and metal-phosphine ligands comprising metals including, but not necessarily limited to palladium, cobalt, and rhodium. The choice of catalysts determines the various reaction conditions imposed. One of ordinary skill in the art, by referring to any of the well-known literature on oxo alcohols, can readily determine the conditions of temperature and pressure that will be needed to hydroformylate the product non-cyclic unsaturated hydrocarbons. An example in addition to U.S. Pat. No. 5,849,960 is EP 0 903 333 A1, incorporated herein by reference.

The product non-cyclic unsaturated hydrocarbons produced as described herein have a variety of uses, including but not necessarily limited to uses in pulp processing, drilling fluids, and machine or metal working. In a preferred embodiment, the product non-cyclic unsaturated hydrocarbons are converted to any of a broad range of surfactants, including nonionic, anionic, cationic, and amphoteric surfactants. The product non-cyclic unsaturated hydrocarbons serve as surfactant intermediates. Specifically, the product non-cyclic unsaturated hydrocarbons serve as the hydrophobic moiety of the surfactant molecule, while the moiety added to the non-cyclic unsaturated hydrocarbons during the conversion process serves as the hydrophile.

The application will be better understood from the following examples, which are illustrative only and should not be construed as limiting the claims. In the following examples, the "non-cyclic-HC:cyclic-HC" ratio is sometimes referred to as the "LO/CO" ratio.

EXAMPLE 1

A heterogeneous rhenium on alumina catalyst comprising 10 wt. % Re was prepared by the pore-volume impregnation of a trilobe alumina extrudate (AX-200, obtained from Criterion Catalyst Company) with an aqueous solution of ammonium perrhenate. 14.41 grams of ammonium perrhenate was dissolved in 100 ml of deionized water. This solution was added to 100 grams of AX-200. The residual water was removed by rotary evaporation. The resulting material was dried at 120° C. and finally calcined at 500° C. to produce the finished catalyst.

The testing unit was a tubular fixed-bed reactor operated in upflow mode. The reactor had an external jacket containing a heat transfer fluid to provide temperature control. The reactor was loaded with 10 ml of the 10% $Re/Al_2O_3$ catalyst. Cyclooctene was promoted with tetrabutyltin (TBT) to give a TBT concentration of 2500 ppm. The cyclooctene solution was fed at a rate of 28 ml/hr, giving an LHSV of 2.8 $hr^{-1}$ based on cyclooctene. 2-Butene was fed at a rate of 65 g/hr. The molar ratio of 2-butene:cyclooctene was 5:1. The reactor was operated at 33° C. and 200 psig nitrogen. Liquid samples were collected and analyzed by gas chromatography (GC). The cyclooctene conversion was found to be 96%. The ratio of 2-butene:cyclooctene was adjusted over the range 5:1 to 20:1 by reducing the cyclooctene flow rate while holding the 2-butene flow rate constant

| Cycloolefin | Linear Olefin | LO/CO Ratio | C12 Selectivity (%) |
| --- | --- | --- | --- |
| COE | 2-Butene | 5:1 | 85 |
| COE | 2-Butene | 10:1 | 91 |
| COE | 2-Butene | 20:1 | 95 |

The foregoing indicates that the feed ratios could be adjusted to favor the desired $C_{12}$ product. Since it was not possible to achieve 100% $C_{12}$ selectivity, a non-cyclic-HC:cyclic-HC ratio (or, LO/CO ratio) of 3:1 was chosen as optimal from a process standpoint. The following table is an expanded version of the above table showing all of the products.

| LO/CO Ratio | C12 Selectivity (%) | C20 Selectivity (%) | C28 Selectivity (%) |
| --- | --- | --- | --- |
| 5:1 | 85 | 14 | 1 |
| 10:1 | 91 | 9 | 0 |
| 20:1 | 95 | 5 | 0 |

EXAMPLE 2

The procedures of Example 1 were repeated using a heterogeneous molybdenum based catalyst (SMO-2, obtained from Criterion Catalyst Company). The following changes were made to the protocol:

1. The catalyst loading was increased to 30 ml.
2. The cyclooctene was diluted in isooctane (1:2 v:v) and no promoter was added.
3. The cyclooctene solution flow rate was 84 ml/hr (28 ml/hr of contained cyclooctene).
4. The reaction temperature was increased to 120° C.

Under these conditions, the cyclooctene conversion was found to be 35%.

The above run with SMO-2 was repeated, but 2500 ppm tetrabutyltin was added to the cyclooctene solution. The cyclooctene conversion increased to 89%. The data below, compared to the data related to the rhenium based catalyst of Example 1, indicates that selectivity is not a function of catalyst, implying that any known metathesis catalyst can be employed with comparable selectivity.

| | | | | |
|---|---|---|---|---|
| Mo-based | 35% | 80% | 16% | 4% |
| Mo-based | 89% | 82% | 16% | 2% |
| Re/Al2O3 | 100% | 85% | 14% | 1% |
| Theory | | 83% | 14% | 3% |

EXAMPLE 3

The procedures of Example 1 were repeated using cyclododecene. As seen from the following Table, the primary selectivity was the same as for cyclooctene, and the conclusion was made that $C_8$ and $C_{12}$ cycloolefins have comparable reactivity.

| Cycloolefin | Linear Olefin | LO/CO Ratio | C16 Selectivity (%) |
|---|---|---|---|
| CDD | 2-Butene | 5:1 | 87 |
| CDD | 2-Butene | 10:1 | 88 |

EXAMPLE 4

Experiments were performed to determine the impact of the non-cyclic-HC selected on the results in ROM. The procedures of Example 1 were followed, except the feeds were changed. Cyclopentene was used as the cyclic-HC, while a mixture of hexene isomers was used as the non-cyclic-HC. The composition of the non-cyclic-HC was determined by GC and is given under the Feed heading in the following Table (wherein "c" refers to "cis," and "t" refers to "trans"). The unreacted hexenes fraction in the product stream from the reactor was also analyzed by GC, and the results are given in the following Table.

| Compound | Feed | Feed | Unreacted Hexene |
|---|---|---|---|
| 1-Hexene | 1.30 | 1.20 | 0.7 |
| c + t-3-Hexene | 22.70 | 23.00 | 18.6 |
| t-2-Hexene | 59.30 | 59.30 | 63.5 |
| c-3-Me-2-Pentene | 0.30 | 0.30 | 0.5 |
| c-2-Hexene | 15.80 | 15.60 | 15.3 |
| t-3-Me-2-Pentene | 0.60 | 0.60 | 1.2 |

The data indicates that the hexene isomers displayed similar reactivities. Based on this data, it was concluded that alpha olefins and internal olefins react at comparable rates.

EXAMPLE 5

The procedures of Example 1 were repeated using 1,5-dimethyl-1,5,-cyclooctadiene (DMCOD). The results are given in the following table:

| Run Time | DMCOD Conversion | C9 | C14 |
|---|---|---|---|
| 1 h | 86% | 44% | 56% |
| 2 h | 71% | 27% | 73% |
| 3 h | 51% | 16% | 84% |

While the DMCOD did cross metathesize, rapid catalyst deactivation occurred Cross metathesis occurred at both double bonds in the DMCOD, leading to the formation of C9 and C14 diolefin products The foregoing results do not necessarily mean that DMCOD is not a suitable cyclic-HC using all catalysts or under all conditions. It may be possible to optimize catalyst and conditions to produce a viable process using DMCOD.

EXAMPLE 6

Grubbs' catalyst [bis(tricyclohexylphosphine)benzylidene ruthenium(IV) dichloride] was purchased from Strem Chemicals. In a glovebox, a Schlenk flask was charged with 50 mg of the Grubbs' catalyst. Dichloromethane (10 ml) was added to dissolve the catalyst. A feed mixture composed of cyclooctene (8 ml), 1-pentene (12 ml), and 2-pentene (12 ml) was added, and the mixture was stirred at room temperature under an inert atmosphere. A sample was taken after 17 hours and analyzed by GC. The cyclooctene conversion was 99%. The carbon number distribution of the resulting products is given in FIG. 1.

The metathesis was also carried out using the 10% $Re/Al_2O_3$ catalyst as described in Example 1. The feed mixture was the same, except that isooctane was used as a solvent. The feed mixture was promoted with 2500 ppm TBT. The carbon number distribution of the resulting products also is given in FIG. 1.

The data illustrated in FIG. 1 indicates that comparable results were achieved using both catalysts.

EXAMPLE 7

The following Table summarizes the data from various experiments and compares the actual data with predicted results:

| Cycloolefin | Linear Olefin | LO/CO Ratio | Primary Selectivity | Predicted Selectivity (%) |
|---|---|---|---|---|
| COE | 2-Butene | 5:1 | 85 | 83 |
| COE | 2-Butene | 10:1 | 91 | 91 |
| COE | 2-Butene | 20:1 | 95 | 95 |
| CDD | 2-Butene | 5:1 | 87 | 83 |
| CDD | 2-Butene | 10:1 | 88 | 91 |

Figure 2:
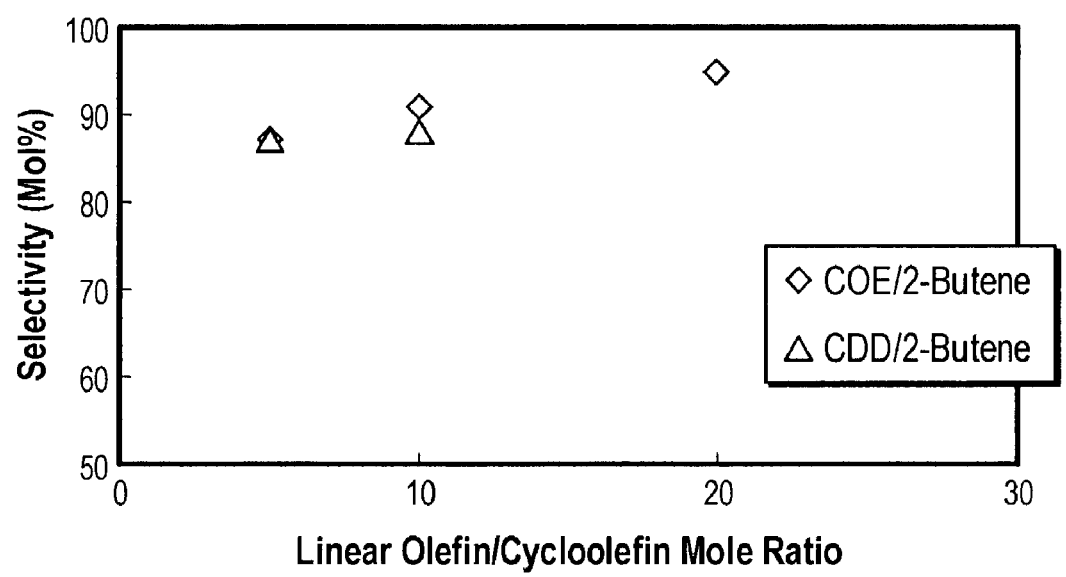
FIG. 2 is a graph of primary product selectivity in ring opening metathesis using different cyclic olefins and non-cyclic hydrocarbons at different ratios (Example 7).
Figure 3:
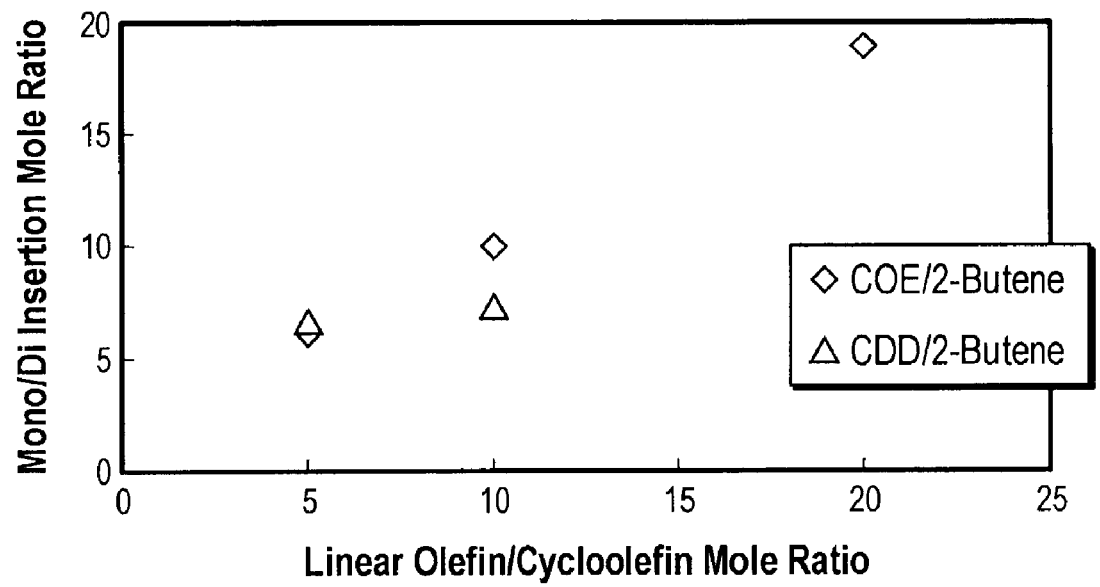
FIG. 3 is a graph of the mono/di insertion mole ratio under the conditions given in FIG. 2.

The foregoing results are depicted in graphic form in FIG. 2. FIG. 3 is a graph of the mono/di insertion mole ratio under the conditions given in FIG. 2. As seen from FIG. 3, the incorporation of a single cyclic-HC molecule in the product (desired) is favored at higher non-cyclic-HC:cyclic-HC ratios.

EXAMPLE 8

Product distribution was predicted for all cases using the following assumptions:
Preferred non-cyclic-HC:cyclic-HC feed ratio is 3:1
cyclic-HC's have equivalent reactivity
non-cyclic-HC's have equivalent reactivity.

The ring opening cross metathesis reaction of a cyclic olefin with an non-non-cyclic olefin will produce a diolefin product. This is the desired reaction. However, it is also possible to incorporate more than one cycloolefin unit into a growing polyene chain. Thus, selectivity is defined on the basis of how many cycloolefin units are incorporated in the final product mixture.

Based on the mechanism of the ring opening metathesis reaction, it is possible to predict the selectivity of a given reaction. The only assumption required is that the cyclic and non-cyclic olefins have equivalent activity. If this assumption is correct, then selectivity should be strictly a function of the feed composition.

Consider the case where the catalyst active site has already reacted with a cycloolefin. At this point, the active site can react with an non-cyclic olefin or another molecule of the cycloolefin. If the non-cyclic olefin is present in a 5:1 molar ratio, then the active site is five times more likely to react with a molecule of the non-cyclic olefin. Thus, five out of six reactions would give the desired cross metathesis product for a molar selectivity of 83%. This value is defined as the primary selectivity. For the 17% of active sites that react with a second molecule of cycloolefin, the next reaction can be with the non-cyclic or cyclic olefin. The probabilities remain the same, so 83% of these reactions will be with the non-cyclic olefin. Thus, 14% (83%×17%) of the product on a molar basis will be a triene in which two cycloolefin units have been incorporated. This value is defined as the secondary selectivity. At this point, there will still be 3% of the active sites that have reacted with a third molecule of cycloolefin. This approach can be continued until all of the active sites have reacted with a molecule of non-cyclic olefin leading to chain termination.

This approach can be applied for any feed ratio. Since the object is to produce dienes in the desired carbon number range, it is expected that the non-cyclic olefin should always be present in excess. The table below shows the predicted selectivities for a variety of non-cyclic:cyclic (LO:CO) feed ratios.

| LO/CO Ratio | Primary Selectivity | Secondary Selectivity | Tertiary Selectivity |
| --- | --- | --- | --- |
| 1:1 | 50% | 25% | 13% |
| 3:1 | 75% | 19% | 4.5% |
| 5:1 | 83% | 14% | 2.5% |
| 10:1 | 91% | 8% | 1% |
| 20:1 | 95% | 5% | 0% |

This method of predicting selectivity was validated by running experiments at varying feed ratios and comparing the experimental results with the predicted values. This comparison revealed that the predictions gave good approximations of the actual selectivities. As a result, this approach was used to construct a spreadsheet model to predict the product distribution for any given feed composition. This model made it possible to evaluate potential feed compositions without running experiments.

The ROM Model results for cyclopentene based on the foregoing assumptions and method are given in the following Table:

| Product | 1:1 1-Pentene/ 2-Pentene | Raff-2 |
| --- | --- | --- |
| C11–C14 | 0.77 | 0.52 |
| C15–C16 | 0.20 | 0.16 |
| C17–C23 | 0.32 | 0.19 |
| Ethylene | 0.08 | 0.13 |
| Propylene | 0.12 | 0.19 |
| Butylenes | 0.32 | 0.57 |
| Pentenes | 0.40 | 0.32 |
| C6–C8 | 1.08 | 0.38 |
| C7–C10 diene | 0.68 | 0.92 |
| Total | 3.95 | 3.38 |
| % C11–C14 | 19.5 | 15.2 |

The ROM Model results for cyclooctene based on the foregoing assumptions are given in the following Table:

| Product | 1:1 1-Pentene/ 2-Pentene | Raff-2 |
| --- | --- | --- |
| C10 | 0.13 | 0.13 |
| C11–C14 | 1.14 | 0.85 |
| C15–C16 | 0.40 | 0 |
| C18–C32 | 0.98 | 0.60 |
| Ethylene | 0.08 | 0.08 |
| Propylene | 0.12 | 0.12 |
| Butylenes | 0.32 | 0.37 |
| Pentenes | 0.40 | 0.20 |
| C6–C8 | 1.08 | 0.24 |
| Total | 4.51 | 2.47 |
| % C11–C14 | 25.3 | 34.4 |

Figure 4:
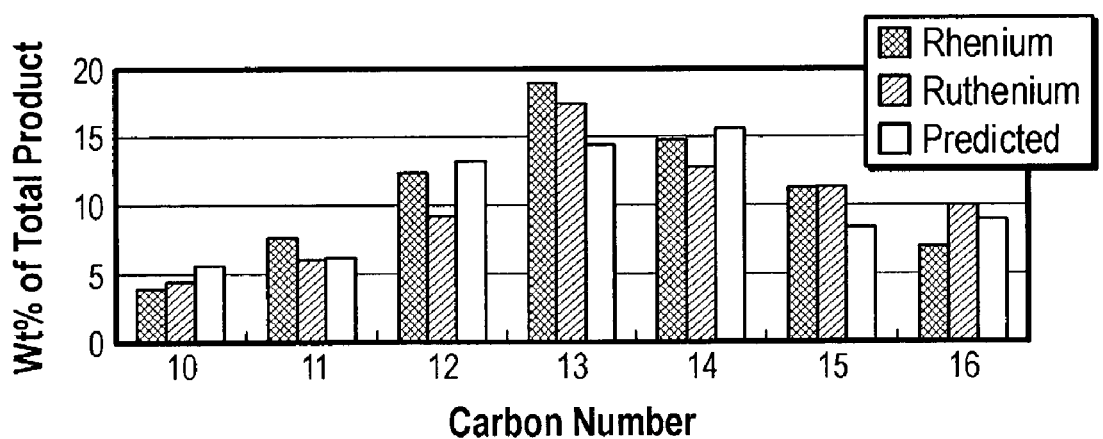
FIG. 4 is a chart comparing model results (Example 8) to experimental results.

The predicted yield of C11–C14 using cyclooctene was approximately twice that using cyclopentene. As seen from FIG. 4, the actual and predicted results were comparable.

EXAMPLE 9

The testing unit was a tubular fixed-bed reactor operated in upflow mode. The reactor had an external jacket containing a heat transfer fluid to provide temperature control. The reactor was loaded with 10 ml of the 10% $Re/Al_2O_3$ catalyst from Example 1. Cyclooctene/isooctane (diluted 1:2) ("COE") was promoted with tetrabutyltin (TBT) to give a TBT concentration of 2500 ppm. The COE was fed at a rate of 83.7 ml/hr, giving an LHSV of 2.8 $hr^{-1}$ based on cyclooctene. 2-Butene was fed at a rate of 60 g/hr. The molar ratio of 2-butene:cyclooctene was 5:1. The reactor was operated at 33° C. and 200 psig nitrogen. Liquid samples were collected and analyzed by gas chromatography (GC). The cyclooctene conversion was found to be 95%. Approximately 4 liters of total product was recovered. The product was then rotovaped at 80° C. and 200 mbar to isolate the $C_{12}$. A total of 530 grams of $C_{12}$ was recovered.

EXAMPLE 10

The $C_{12}$ from Example 9 was hydroformylated in a 500 cc stainless steel zipperclave. The reactor (zipperclave) was purged with nitrogen, charged with syngas, $H_2/CO$, 2:1, and heated to the target temperature. In order to keep the gas cap of the reactor at constant composition, the makeup gas was $H_2/CO$, 3:1, assumed to be the stoichiometry of the gas consumed in the reaction. A cobalt based hydroformylation catalyst was dissolved in the $C_{12}$. KOH was dissolved in decanol. These solutions were then charged to the zipperclave with a syringe. Samples were taken during the reaction at 0, 30, 60, 120, 180 and 240 minutes. Both internal and external GC standards were used for analysis of the samples. The conventional internal standard, tridecane, was found to be unsatisfactory due to overlap with the diene starting material.

The $C_{12}$ feed appeared to be about 93% pure. The main impurities were cyclooctane, cyclooctene, and C20 triolefin. In each experiment the cyclooctene was slowly hydroformylated to cyclooctylmethanol; this reaction was not further quantified.

Three experiments were conducted. The conditions for each experiment and the results are summarized in Table 1:

TABLE 1

Summary of Results

|  | Exp. 1 | Exp. 2 | Exp. 3 |
| --- | --- | --- | --- |
| sec-UH | dodecadiene | dodecadiene | dodecadiene |
| % Wt in Rxn Mix | 98.6 | 58.5 | 31.4 |
| Cobalt source | Cobalt Carbonyl | Cobalt Carbonyl | Cobalt Carbonyl |
| % Wt Co in Rxn Mix | 0.1 | 0.1 | 0.05 |
| RM-17/Co | 1.39 | 1.15 | 1.13 |
| KOH/Co | 0 | 0.55 | 0.55 |
| Co-solvent | none | decanol | decanol |
| % Wt in Rxn Mix |  | 40.2 | 66.2 |
| Temperature (° C.) | 180 | 180 | 180 |
| Pressure (Psig) | 1050 | 1050 | 1050 |
| H2/CO Ratio | 2 | 2 | 2 |
| Reaction Time (hrs) | 4 | 5 | 5 |
| Olefin Conversion | 99 | 90 | 80 |
| Products derived from dodecadiene |  |  |  |
| Tridecanol, linear + branched (%) | 58 | 45 | 37 |
| Linearity (%) | 71 | 75 | 71 |
| Sum of tridecyl formate, tridecanal, and tridecenol isomers (%) | 3 | 3 | 15 |
| Total C13 products (%) | 61 | 48 | 52 |
| Dodecane | 6 | 8.5 | 4 |

From the foregoing, it was determined that dodecadiene produced by cross metathesis could be hydroformylated to primarily tridecanol.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method for making unsaturated hydrocarbons, said method comprising:

providing a mixture comprising one or more cyclic unsaturated hydrocarbons and an excess of one or more non-cyclic unsaturated hydrocarbons wherein the molar ratio of non-cyclic unsaturated hydrocarbons to cyclic unsaturated hydrocarbons is from about 5:1 to about 3:1, said cyclic unsaturated hydrocarbons having a ΔG of less than 0 at 25° C. and comprising a ring structure comprising x carbon atoms and;

exposing said mixture to conditions effective to cross metathesize said one or more cyclic unsaturated hydrocarbons with said one or more non-cyclic unsaturated hydrocarbons to produce primarily non-cyclic unsaturated product hydrocarbons comprising a single molecule of said cyclic unsaturated hydrocarbons and having more than x carbon atoms.

2. The method of claim 1 wherein said unsaturated product hydrocarbons comprise from 10 to 16 carbon atoms.

3. The method of claim 1 wherein said unsaturated product hydrocarbons comprise from 11 to 14 carbon atoms.

4. The method of claim 1 wherein said unsaturated product hydrocarbons comprise 15 and 16 carbon atoms.

5. The method of claim 1 wherein said non-cyclic unsaturated hydrocarbons comprise a single unsaturated carbon-carbon bond, a first remainder of said carbon backbone to the left of said unsaturated carbon-carbon bond and a second remainder of said carbon backbone to the right of said unsaturated carbon-carbon bond, said first remainder and said second remainder of said carbon backbone comprising the same number of carbon atoms.

6. The method of claim 1 wherein said cyclic unsaturated hydrocarbons comprise from 8 to 12 carbon atoms.

7. The method of claim 1 wherein said ring structure of said cyclic unsaturated hydrocarbons comprises a single unsaturated carbon—carbon bond.

8. The method of claim 6 wherein said ring structure of said cyclic unsaturated hydrocarbons comprises a single unsaturated carbon—carbon bond.

9. The method of claim 1 wherein said ring structure comprises one or more substituents having a size, type, and location that does not interfere with cross metathesis.

10. The method of claim 8 wherein said ring structure comprises one or more substituents having a size, type, and location that does not interfere with cross metathesis.

11. The method of claim 1 wherein said cyclic unsaturated hydrocarbons have a ΔG of −1 kcal/mol or less at 25° C.

12. The method of claim 1 wherein said cyclic unsaturated hydrocarbons have a ΔG of −2 kcal/mol or less at 25° C.

13. The method of claim 1 wherein said cyclic unsaturated hydrocarbons have a ΔG of −3 kcal/mol or less at 25° C.

14. The method of claim 1 wherein said non-cyclic unsaturated hydrocarbons have from about 4 to about 8 carbon atoms.

15. The method of claim 14 wherein said non-cyclic unsaturated hydrocarbons have from about 4 to about 6 carbon atoms.

16. The method of claim 15 wherein said non-cyclic unsaturated hydrocarbon is 2-butene.

17. The method of claim 1 wherein said providing a mixture comprises feeding said cyclic unsaturated hydrocarbons to a vessel at a liquid hourly space velocity (LHSV) of from 1 hr−1 to 10 hr−1.

18. The method of claim 1 wherein said conditions comprise:
feeding said cyclic unsaturated hydrocarbons to a vessel at a liquid hourly space velocity (LHSV) of about 2 hr−1;
wherein said exposing occurs at a pressure of at least 15 psig in the presence of a ROM catalyst comprising a metal selected from the group consisting of Re and Mo;
wherein, when said metal is Re, said exposing occurs at a temperature of from about 0° C. to about 100° C.; and
wherein, when said metal is Mo, said exposing occurs at a temperature of from about 50° C. to about 200° C.

19. The method of claim 1 further comprising hydrogenating said unsaturated product hydrocarbons to produce hydrogenated unsaturated product hydrocarbons.

20. The method of claim 10 further comprising hydrogenating said unsaturated product hydrocarbons to produce hydrogenated unsaturated product hydrocarbons.

21. The method of claim 1 further comprising hydroformylating said unsaturated product hydrocarbons.

22. The method of claim 10 further comprising hydroformylating said unsaturated product hydrocarbons.

23. The method of claim 19 further comprising hydroformylating said unsaturated product hydrocarbons.

24. The method of claim 20 further comprising hydroformylating said unsaturated product hydrocarbons.

25. The method of claim 1 wherein said unsaturated product hydrocarbons comprise from 1 to 2 branches having from 1 to 2 carbon atoms.

26. The method of claim 1 wherein said unsaturated product hydrocarbons comprise a single methyl substituent.

27. The method of claim 1 wherein said exposing occurs in a catalytic distillation column.

28. The method of claim 1 wherein said conditions comprise a ring opening metathesis ("ROM") catalyst.

29. A method for making unsaturated hydrocarbons comprising more than 8 carbon atoms, said method comprising:
providing a mixture comprising cyclooctene and an excess of one or more non-cyclic unsaturated hydrocarbons wherein the molar ratio of non-cyclic unsaturated hydrocarbons to cyclic unsaturated hydrocarbons is from about 5:1 to about 3:1; and,
exposing said mixture to conditions effective to cross metathesize said cyclooctene with said one or more non-cyclic unsaturated hydrocarbons to produce primarily non-cyclic unsaturated product hydrocarbons comprising a single molecule of said cyclooctene, said product non-cyclic unsaturated hydrocarbons having more than 8 carbon atoms.

30. The method of claim 29 wherein said one or more non-cyclic unsaturated hydrocarbons comprise a by-product from a refinery process.

31. The method of claim 29 wherein said conditions comprise a ROM catalyst.

32. The method of claim 31 wherein said cyclooctene comprises a single unsaturated carbon—carbon bond.

33. The method of claim 32 wherein said cyclooctene comprises one or more substituents having a size, type, and location that does not interfere with cross metathesis.

34. The method of claim 33 wherein said cyclooctene comprises one or more methyl substituents.

35. The method of claim 33 wherein said cyclooctene comprises one methyl substituent.

36. The method of claim 30 wherein said byproduct of a refinery stream comprises the C5 cut from a fluid catalytic cracker.

37. The method of claim 30 wherein said byproduct of a refinery stream comprises raffinate from a C4 stream from an olefin cracker.

38. The method of claim 30 wherein said byproduct of a refinery stream comprises the C5 cut from a fluid catalytic cracker.

39. The method of claim 30 wherein said byproduct of a refinery stream comprises raffinate from a C4 stream from an olefin cracker.

40. The method of claim 37 wherein, before providing said mixture, said raffinate is isomerized to produce primarily 2-butene as said non-cyclic unsaturated hydrocarbon.

41. The method of claim 39 wherein, before providing said mixture, said raffinate is isomerized to produce primarily 2-butene as said non-cyclic unsaturated hydrocarbon.

42. The method of claim 29 wherein said non-cyclic unsaturated hydrocarbons have from about 4 to about 8 carbon atoms.

43. The method of claim 42 wherein said non-cyclic unsaturated hydrocarbons have from about 4 to about 6 carbon atoms.

44. The method of claim 43 wherein said non-cyclic unsaturated hydrocarbon is 2-butene.

45. The method of claim 31 wherein said ROM catalyst is heterogeneous.

46. The method of claim 31 wherein said ROM catalyst comprises one or more metals selected from the group consisting of Cr, Mo, W, Mn, Tc, Re, Fe, Ru, Os.

47. The method of claim 31 wherein said ROM catalyst comprises a metal selected from the group consisting of Mo, W, Re, and Ru.

48. The method of claim 31 wherein said ROM catalyst comprises a metal selected from the group consisting of Re and Ru.

49. The method of claim 31 wherein said ROM catalyst is Re/Al2O3 comprising Re at a concentration of from 1 to 20 wt %.

50. The method of claim 49 wherein said concentration of said Re is from 5 to 12 wt. %.

51. The method of claim 30 wherein said conditions comprise a ROM catalyst comprising Re/Al2O3 comprising Re at a concentration of from about 5 to about 12 wt. %.

52. The method of claim 47 further comprising treating said ROM catalyst with a promoter.

53. The method of claim 51 further comprising treating said ROM catalyst with a promoter.

54. The method of claim 52 wherein said treating said ROM catalyst comprises exposing said ROM catalyst to said promoter before said exposing said mixture to said conditions effective to cross metathesize said cyclooctene with said one or more non-cyclic unsaturated hydrocarbons.

55. The method of claim 53 wherein said treating comprises feeding said promoter to a reactor with said cyclooctene.

56. The method of claim 55 wherein said promoter comprises one or more alkylated elements selected from the group consisting of B, Al, Ga, In, Tl, C, Si, Ge, Sn, Pb, N, P, As, Sb, and Bi.

57. The method of claim 56 wherein said one or more alkylated elements are selected from the group consisting of B, Al, Sn, and Si.

58. The method of claim 55 wherein said promoter is selected from the group consisting of alkylboranes and alkyltins.

59. The method of claim 55 wherein said promoter is tetrabutyltin.

60. The method of claim 55 wherein said promoter is present in said cyclooctene at a concentration of from 1 ppm to 10,000 ppm.

61. The method of claim 60 wherein said promoter is present in said cyclooctene at a concentration of 2500 ppm.

62. The method of claim 31 further comprising hydrogenating said unsaturated product hydrocarbons to produce hydrogenated unsaturated product hydrocarbons.

63. The method of claim 61 further comprising hydrogenating said unsaturated product hydrocarbons to produce hydrogenated unsaturated product hydrocarbons.

64. The method of claim 31 further comprising hydroformylating said unsaturated product hydrocarbons.

65. The method of claim 61 further comprising hydroformylating said unsaturated product hydrocarbons.

66. The method of claim 63 further comprising hydroformylating said unsaturated product hydrocarbons.

67. The method of claim 31 wherein said exposing occurs in a catalytic distillation column.

68. The method of claim 29 wherein said non-cyclic unsaturated hydrocarbons comprise a single unsaturated carbon—carbon bond, a first remainder of said carbon backbone to the left of said unsaturated carbon—carbon bond and a second remainder of said carbon backbone to the right of said unsaturated carbon—carbon bond, said first remainder and said second remainder of said carbon backbone comprising the same number of carbon atoms.

69. A method for making unsaturated hydrocarbons comprising more than 12 carbon atoms, said method comprising:
providing a mixture comprising cyclododecene and an excess of one or more non-cyclic unsaturated hydrocarbons wherein the molar ratio of non-cyclic unsaturated hydrocarbons to cyclic unsaturated hydrocarbons is from about 5:1 to about 3:1; and,
exposing said mixture to conditions effective to cross metathesize said cyclododecene with said one or more non-cyclic unsaturated hydrocarbons to produce primarily non-cyclic unsaturated product hydrocarbons comprising a single molecule of said cyclododecene, said product non-cyclic unsaturated hydrocarbons having more than 12 carbon atoms.

70. The method of claim 69 wherein said one or more non-cyclic unsaturated hydrocarbons comprise a by-product from a refinery process.

71. The method of claim 69 wherein said conditions comprise a ROM catalyst.

72. The method of claim 71 wherein said cyclododecene comprises a single unsaturated carbon—carbon bond.

73. The method of claim 72 wherein said cyclododecene comprises one or more substituents having a size, type, and location that does not interfere with cross metathesis.

74. The method of claim 73 wherein said cyclododecene comprises one or more methyl substituents.

75. The method of claim 73 wherein said cyclododecene comprises one methyl substituent.

76. The method of claim 70 wherein said byproduct of a refinery stream comprises the C5 cut from a fluid catalytic cracker.

77. The method of claim 70 wherein said byproduct of a refinery stream comprises raffinate from a C4 stream from an olefin cracker.

78. The method of claim 70 wherein said byproduct of a refinery stream comprises the C5 cut from a fluid catalytic cracker.

79. The method of claim 70 wherein said byproduct of a refinery stream comprises raffinate from a C4 stream from an olefin cracker.

80. The method of claim 77 wherein, before providing said mixture, said raffinate is isomerized to produce primarily 2-butene as said non-cyclic unsaturated hydrocarbon.

81. The method of claim 77 wherein, before providing said mixture, said raffinate is isomerized to produce primarily 2-butene as said non-cyclic unsaturated hydrocarbon.

82. The method of claim 69 wherein said non-cyclic unsaturated hydrocarbons have from about 4 to about 8 carbon atoms.

83. The method of claim 82 wherein said non-cyclic unsaturated hydrocarbons have from about 4 to about 6 carbon atoms.

84. The method of claim 83 wherein said non-cyclic unsaturated hydrocarbon is 2-butene.

85. The method of claim 71 wherein said ROM catalyst is heterogeneous.

86. The method of claim 71 wherein said ROM catalyst comprises one or more metals selected from the group consisting of Cr, Mo, W, Mn, Tc, Re, Fe, Ru, Os.

87. The method of claim 71 wherein said ROM catalyst comprises a metal selected from the group consisting of Mo, W, Re, and Ru.

88. The method of claim 71 wherein said ROM catalyst comprises a metal selected from the group consisting of Re and Ru.

89. The method of claim 89 wherein said ROM catalyst is Re/Al2O3 comprising Re at a concentration of from 1 to 20 wt %.

90. The method of claim 89 wherein said concentration of said Re is from 5 to 12 wt. %.

91. The method of claim 70 wherein said conditions comprise a ROM catalyst comprising Re/Al2O3 comprising Re at a concentration of from about 5 to about 12 wt. %.

92. The method of claim 81 wherein said conditions comprise a ROM catalyst comprising Re/Al2O3 comprising Re at a concentration of from about 5 to about 12 wt. %.

93. The method of claim 85 further comprising treating said ROM catalyst with a promoter.

94. The method of claim 92 further comprising treating said ROM catalyst with a promoter.

95. The method of claim 92 wherein said treating said ROM catalyst comprises exposing said ROM catalyst to said promoter before said exposing said mixture to said conditions effective to cross metathesize said cyclododecene with said one or more non-cyclic unsaturated hydrocarbons.

96. The method of claim 94 wherein said treating comprises feeding said promoter to a reactor with said cyclododecene.

97. The method of claim 93 wherein said promoter comprises one or more alkylated elements selected from the group consisting of B, Al, Ga, In, Tl, C, Si, Ge, Sn, Pb, N, P, As, Sb, and Bi.

98. The method of claim 93 wherein said one or more alkylated elements are selected from the group consisting of B, Al, Sn, and Si.

99. The method of claim 93 wherein said promoter is selected from the group consisting of alkylboranes and alkyltins.

100. The method of claim 93 wherein said promoter is tetrabutyltin.

101. The method of claim 96 wherein said promoter is selected from the group consisting of alkylboranes and alkyltins.

102. The method of claim 96 wherein said promoter is tetrabutyltin.

103. The method of claim 93 wherein said promoter is present in said cyclododecene at a concentration of from 1 ppm to 10,000 ppm.

104. The method of claim 102 wherein said promoter is present in said cyclododecene at a concentration of 2500 ppm.

105. The method of claim 69 further comprising hydrogenating said unsaturated product hydrocarbons to produce hydrogenated unsaturated product hydrocarbons.

106. The method of claim 73 further comprising hydrogenating said unsaturated product hydrocarbons to produce hydrogenated unsaturated product hydrocarbons.

107. The method of claim 75 further comprising hydrogenating said unsaturated product hydrocarbons to produce hydrogenated unsaturated product hydrocarbons.

108. The method of claim 79 further comprising hydrogenating said unsaturated product hydrocarbons to produce hydrogenated unsaturated product hydrocarbons.

109. The method of claim 104 further comprising hydrogenating said unsaturated product hydrocarbons to produce hydrogenated unsaturated product hydrocarbons.

110. The method of claim 69 further comprising hydroformylating said unsaturated product hydrocarbons.

111. The method of claim 105 further comprising hydroformylating said unsaturated product hydrocarbons.

112. The method of claim 106 further comprising hydroformylating said unsaturated product hydrocarbons.

113. The method of claim 107 further comprising hydroformylating said unsaturated product hydrocarbons.

114. The method of claim 108 further comprising hydroformylating said unsaturated product hydrocarbons.

115. The method of claim 109 further comprising hydroformylating said unsaturated product hydrocarbons.

116. The method of claim 69 wherein said exposing occurs in a catalytic distillation column.

117. The method of claim 69 wherein said non-cyclic unsaturated hydrocarbons comprise a single unsaturated carbon—carbon bond, a first remainder of said carbon backbone to the left of said unsaturated carbon—carbon bond and a second remainder of said carbon backbone to the right of said unsaturated carbon—carbon bond, said first remainder and said second remainder of said carbon backbone comprising the same number of carbon atoms.

118. A method for making unsaturated hydrocarbons comprising more than 8 carbon atoms, said method comprising:
cyclodimerizing butadiene to produce cyclooctene;
providing a mixture comprising cyclooctene and an excess of one or more non-cyclic unsaturated hydrocarbons wherein the molar ratio of non-cyclic unsaturated hydrocarbons to cyclooctene is from about 5:1 to about 3:1; and,
exposing said mixture to conditions effective to cross metathesize said cyclooctene with said one or more non-cyclic unsaturated hydrocarbons to produce primarily non-cyclic unsaturated product hydrocarbons comprising a single molecule of said cyclooctene, said product non-cyclic unsaturated hydrocarbons having more than 8 carbon atoms.

119. The method of claim 118 wherein said one or more non-cyclic unsaturated hydrocarbons comprise a by-product from a refinery process.

120. The method of claim 118 wherein said conditions comprise a ROM catalyst.

121. The method of claim 120 wherein said cyclooctene comprises a single unsaturated carbon—carbon bond.

122. The method of claim 121 wherein said cyclooctene comprises one or more substituents having a size, type, and location that does not interfere with cross metathesis.

123. The method of claim 122 wherein said cyclooctene comprises one or more methyl substituents.

124. The method of claim 122 wherein said cyclooctene comprises one methyl substituent.

125. The method of claim 122 wherein said byproduct of a refinery stream comprises the C5 cut from a fluid catalytic cracker.

126. The method of claim 119 wherein said byproduct of a refinery stream comprises raffinate from a C4 stream from an olefin cracker.

127. The method of claim 119 wherein said byproduct of a refinery stream comprises the C5 cut from a fluid catalytic cracker.

128. The method of claim 119 wherein said byproduct of a refinery stream comprises raffinate from a C4 stream from an olefin cracker.

129. The method of claim 119 wherein said byproduct of a refinery stream comprises the C5 cut from a fluid catalytic cracker.

130. The method of claim 119 wherein said byproduct of a refinery stream comprises raffinate from a C4 stream from an olefin cracker.

131. The method of claim 126 wherein, before providing said mixture, said raffinate is isomerized to produce primarily 2-butene as said non-cyclic unsaturated hydrocarbon.

132. The method of claim 128 wherein, before providing said mixture, said raffinate is isomerized to produce primarily 2-butene as said non-cyclic unsaturated hydrocarbon.

133. The method of claim 130 wherein, before providing said mixture, said raffinate is isomerized to produce primarily 2-butene as said non-cyclic unsaturated hydrocarbon.

134. The method of claim 118 wherein said non-cyclic unsaturated hydrocarbon has from about 4 to about 8 carbon atoms.

135. The method of claim 134 wherein said non-cyclic unsaturated hydrocarbon has from about 4 to about 6 carbon atoms.

136. The method of claim 135 wherein said noncyclic unsaturated hydrocarbon is 2-butene.

137. The method of claim 120 wherein said ROM catalyst is heterogeneous.

138. The method of claim 120 wherein said ROM catalyst comprises one or more metals selected from the group consisting of Cr, Mo, W, Mn, Tc, Re, Fe, Ru, Os.

139. The method of claim 120 wherein said ROM catalyst comprises a metal selected from the group consisting of Mo, W, Re, and Ru.

140. The method of claim 120 wherein said ROM catalyst comprises a metal selected from the group consisting of Re and Ru.

141. The method of claim 137 wherein said ROM catalyst is Re/Al2O3 comprising Re at a concentration of from 1 to 20 wt %.

142. The method of claim 141 wherein said concentration of said Re is from 5 to 12 wt. %.

143. The method of claim 138 further comprising treating said ROM catalyst with a promoter.

144. The method of claim 141 further comprising treating said ROM catalyst with a promoter.

145. The method of claim 143 wherein said treating said ROM catalyst comprises exposing said ROM catalyst to said promoter before said exposing said mixture to said conditions effective to cross metathesize said cyclooctene with said one or more non-cyclic unsaturated hydrocarbons.

146. The method of claim 144 wherein said treating comprises feeding said promoter to a reactor with said cyclooctene.

147. The method of claim 143 wherein said promoter comprises one or more alkylated elements selected from the group consisting of B, Al, Ga, In, Tl, C, Si, Ge, Sn, Pb, N, P, As, Sb, and Bi.

148. The method of claim 147 wherein said one or more alkylated elements are selected from the group consisting of B, Al, Sn, and Si.

149. The method of claim 143 wherein said promoter is selected from the group consisting of alkylboranes and alkyltins.

150. The method of claim 149 wherein said promoter is an alkyltin.

151. The method of claim 150 wherein said promoter is tetrabutyltin.

152. The method of claim 147 wherein said promoter is present in said cyclooctene at a concentration of from 1 ppm to 10,000 ppm.

153. The method of claim 151 wherein said promoter is present in said cyclooctene at a concentration of 2500 ppm.

154. The method of claim 120 further comprising hydrogenating said unsaturated product hydrocarbons to produce hydrogenated unsaturated product hydrocarbons.

155. The method of claim 120 further comprising hydrogenating said unsaturated product hydrocarbons to produce hydrogenated unsaturated product hydrocarbons.

156. The method of claim 120 further comprising hydroformylating said unsaturated product hydrocarbons.

157. The method of claim 154 further comprising hydroformylating said unsaturated product hydrocarbons.

158. The method of claim 155 further comprising hydroformylating said unsaturated product hydrocarbons.

159. The method of claim 120 wherein said exposing occurs in a catalytic distillation column.

160. The method of claim 120 wherein said non-cyclic unsaturated hydrocarbons comprise a single unsaturated carbon—carbon bond, a first remainder of said carbon backbone to the left of said unsaturated carbon—carbon bond and a second remainder of said carbon backbone to the right of said unsaturated carbon—carbon bond, said first remainder and said second remainder of said carbon backbone comprising the same number of carbon atoms.

161. A method for making unsaturated hydrocarbons comprising more than 12 carbon atoms, said method comprising:
cyclotrimerizing butadiene to produce cyclododecene;
providing a mixture comprising said cyclododecene and an excess of one or more non-cyclic unsaturated hydrocarbons wherein the molar ratio of non-cyclic unsaturated hydrocarbons to cyclododecene is from about 5:1 to about 3:1; and,
exposing said mixture to conditions effective to cross metathesize said cyclododecene with said one or more non-cyclic unsaturated hydrocarbons to produce primarily non-cyclic unsaturated product hydrocarbons comprising a single molecule of said cyclododecene, said product non-cyclic unsaturated hydrocarbons having more than 12 carbon atoms.

162. The method of claim 161 wherein said one or more non-cyclic unsaturated hydrocarbons comprise a by-product from a refinery process.

163. The method of claim 162 wherein said conditions comprise a ROM catalyst.

164. The method of claim 163 wherein said cyclododecene comprises a single unsaturated carbon—carbon bond.

165. The method of claim 164 wherein said cyclododecene comprises one or more substituents having a size, type, and location that does not interfere with cross metathesis.

166. The method of claim 165 wherein said cyclododecene comprises one methyl substituent.

167. The method of claim 162 wherein said byproduct of a refinery stream comprises the C5 cut from a fluid catalytic cracker.

168. The method of claim 162 wherein said byproduct of a refinery stream comprises raffinate from a C4 stream from an olefin cracker.

169. The method of claim 166 wherein said byproduct of a refinery stream comprises the C5 cut from a fluid catalytic cracker.

170. The method of claim 166 wherein said byproduct of a refinery stream comprises raffinate from a C4 stream from an olefin cracker.

171. The method of claim 168 wherein, before providing said mixture, said raffinate is isomerized to produce primarily 2-butene as said non-cyclic unsaturated hydrocarbon.

172. The method of claim 170 wherein, before providing said mixture, said raffinate is isomerized to produce primarily 2-butene as said non-cyclic unsaturated hydrocarbon.

173. The method of claim 161 wherein said non-cyclic unsaturated hydrocarbon has from about 4 to about 8 carbon atoms.

174. The method of claim 173 wherein said non-cyclic unsaturated hydrocarbon has from about 4 to about 6 carbon atoms.

175. The method of claim 174 wherein said non-cyclic unsaturated hydrocarbon is 2-butene.

176. The method of claim 163 wherein said ROM catalyst comprises one or more metals selected from the group consisting of Cr, Mo, W, Mn, Tc, Re, Fe, Ru, Os.

177. The method of claim 163 wherein said ROM catalyst comprises a metal selected from the group consisting of Mo, W, Re, and Ru.

178. The method of claim 163 wherein said ROM catalyst comprises a metal selected from the group consisting of Re and Ru.

179. The method of claim 163 wherein said ROM catalyst is a heterogeneous catalyst comprising a metal on a support, wherein:
when said metal is selected from the group consisting of Mo and Re, said support is aluminum oxide; and,
when said metal is W, said support silicon oxide.

180. The method of claim 163 wherein said ROM catalyst is Re/Al2O3 comprising Re at a concentration of from 1 to 20 wt %.

181. The method of claim 180 wherein said concentration of said Re is from 5 to 12 wt. %.

182. The method of claim 163 further comprising treating said ROM catalyst with a promoter.

183. The method of claim 181 further comprising treating said ROM catalyst with a promoter.

184. The method of claim 183 wherein said treating comprises feeding said promoter to a reactor with said cyclododecene.

185. The method of claim 184 wherein said promoter comprises one or more alkylated elements selected from the group consisting of B, Al, Ga, In, Tl, C, Si, Ge, Sn, Pb, N, P, As, Sb, and Bi.

186. The method of claim 184 wherein said one or more alkylated elements are selected from the group consisting of B, Al, Sn, and Si.

187. The method of claim 184 wherein said promoter is selected from the group consisting of alkylboranes and alkyltins.

188. The method of claim 184 wherein said promoter is tetrabutyltin.

189. The method of claim 188 wherein said promoter is present in said cyclooctene at a concentration of 2500 ppm.

190. The method of claim 161 further comprising hydrogenating said unsaturated product hydrocarbons to produce hydrogenated unsaturated product hydrocarbons.

191. The method of claim 189 further comprising hydrogenating said unsaturated product hydrocarbons to produce hydrogenated unsaturated product hydrocarbons.

192. The method of claim 161 further comprising hydroformylating said unsaturated product hydrocarbons.

193. The method of claim 191 further comprising hydroformylating said unsaturated product hydrocarbons.

194. The method of claim 161 wherein said exposing occurs in a catalytic distillation column.

195. The method of claim 166 wherein said methyl substituent is located on a saturated carbon atom.

* * * * *